United States Patent [19]

Imamura et al.

[11] Patent Number: 4,776,693
[45] Date of Patent: Oct. 11, 1988

[54] FOREIGN SUBSTANCE INSPECTING SYSTEM INCLUDING A CALIBRATION STANDARD

[75] Inventors: Kazunori Imamura, Tokyo; Akikazu Tanimoto; Yukio Kakizaki, both of Yokohama, all of Japan

[73] Assignee: Nippon Kogaku K. K., Tokyo, Japan

[21] Appl. No.: 120,231

[22] Filed: Nov. 12, 1987

Related U.S. Application Data

[63] Continuation of Ser. No. 729,969, May 3, 1985, abandoned.

[30] Foreign Application Priority Data

May 11, 1984 [JP] Japan .................. 59-94057
Jun. 6, 1984 [JP] Japan .................. 59-116206

[51] Int. Cl.$^4$ .................................. G01N 21/88
[52] U.S. Cl. .................. 356/243; 356/237
[58] Field of Search ............. 356/237, 243; 250/252.1

[56] References Cited

U.S. PATENT DOCUMENTS

4,386,850  6/1983  Leahy ......................... 356/243
4,468,120  8/1984  Tanimoto et al. ............. 356/237

OTHER PUBLICATIONS

"Design of a Pattern on a Photomask-Like Physical Standard for Evaluation and Calibration of Linewidth-Measuring Systems", SWYT, Solid State Technology, 1-1978, pp. 35-42.

Primary Examiner—Vincent P. McGraw
Assistant Examiner—S. A. Turner
Attorney, Agent, or Firm—Shapiro and Shapiro

[57] ABSTRACT

A system for placing thereron an object to be inspected, scanning the surface of the object to be inspected by a light spot and inspecting a foreign substance on the basis of light information produced by the foreign substance on the surface of the object to be inspected includes light information producing means including a member for producing light information substantially similar to the light information produced by the foreign substance, and means for disposing the member on a surface substantially identical to the surface of the object to be inspected placed on the system.

8 Claims, 5 Drawing Sheets

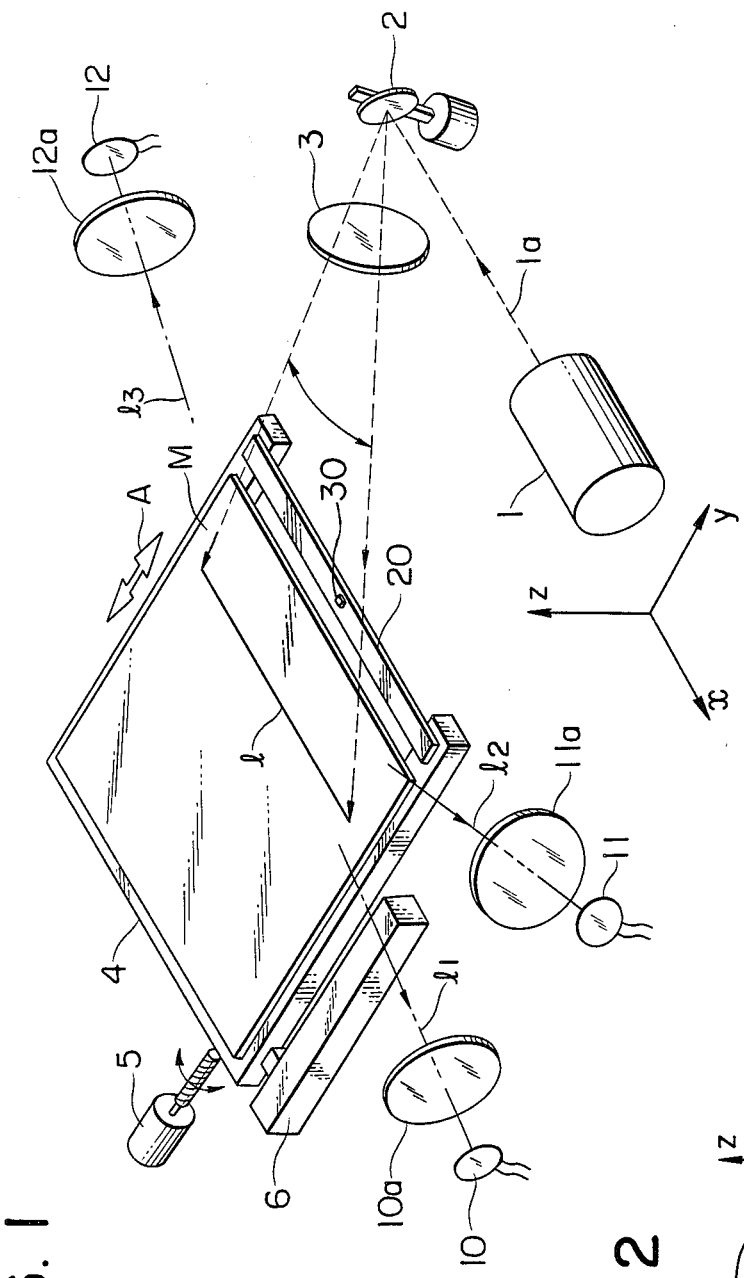
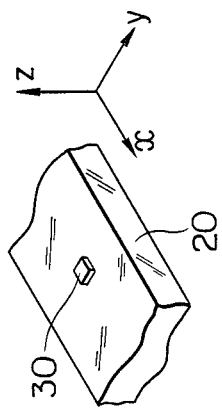
FIG. 1
FIG. 2

FOREIGN SUBSTANCE INSPECTING SYSTEM INCLUDING A CALIBRATION STANDARD

This is a continuation application of U.S. Ser. No. 729,969 filed May 3, 1985, now abandoned.

BACKGROUND OF THE INVENTION

1. Field of the Invention

This invention relates to an apparatus for inspecting a foreign substance such as minute dust or a flaw adhering to an object to be inspected by the scanning of a light beam, and in particular to a system and method for inspecting a foreign substance adhering to a photomask or a reticle used for the manufacture of semiconductor integrated circuits.

2. Description of the Prior Art

A foreign substance (such as minute dust or a flaw) adhering to a photomask or a reticle (hereinafter typically referred to as a mask) for the manufacture of IC or LSI, like a pattern such as chromium intercepting the light for exposure, is transferred to a photoresist layer on a semiconductor wafer (hereinafter referred to as the wafer). This means that unsatisfactory operation of the manufactured semiconductor integrated circuit or a significant reduction in yield may result. Thus, as disclosed, for example, in U.S. Pat. No. 4,468,120, there is proposed an apparatus in which a light beam such as laser light is scanned on a mask and the light information from a foreign substance, particularly, scattered light of weak directionality, is photoelectrically detected by photoelectric detectors disposed in a plurality of directions and on the basis of the photoelectric signals thereof, the presence of the adherence of a foreign substance, the state of adherence thereof, the size of the foreign substance, etc. are automatically inspected. The accuracy of foreign substance detection in apparatus of this type is determined by the intensity of the laser light, the spot size of the laser light on the mask or the sensitivity of the photoelectric detectors (for example, photomultipliers). If this foreign substance detection accuracy is not constant during each inspection, the result of the inspection will vary greatly for each mask in spite of the fact that foreign substances of the same size and shape adhere to different masks.

SUMMARY OF THE INVENTION

It is an object of the present invention to provide a foreign substance inspecting system whose foreign substance detection accuracy is stabilized by a simple construction.

According to the present invention, in a system wherein an object to be inspected is scanned by a light beam such as laser light and a photoelectric signal corresponding to light information (such as scattered light, reflected light or diffracted light) produced by the light beam is put out from the irradiated portion on the object to be inspected, a member for producing light information similar to the light information produced from a foreign substance is provided on a plane substantially identical to the surface of the object to be inspected.

BRIEF DESCRIPTION OF THE DRAWINGS

FIG. 1 is a perspective view schematically showing the construction of the present invention.

FIG. 2 is a fragmentary perspective view showing a reference pattern according to a first embodiment of the present invention.

DESCRIPTION OF THE PREFERRED EMBODIMENTS

Figure 3:
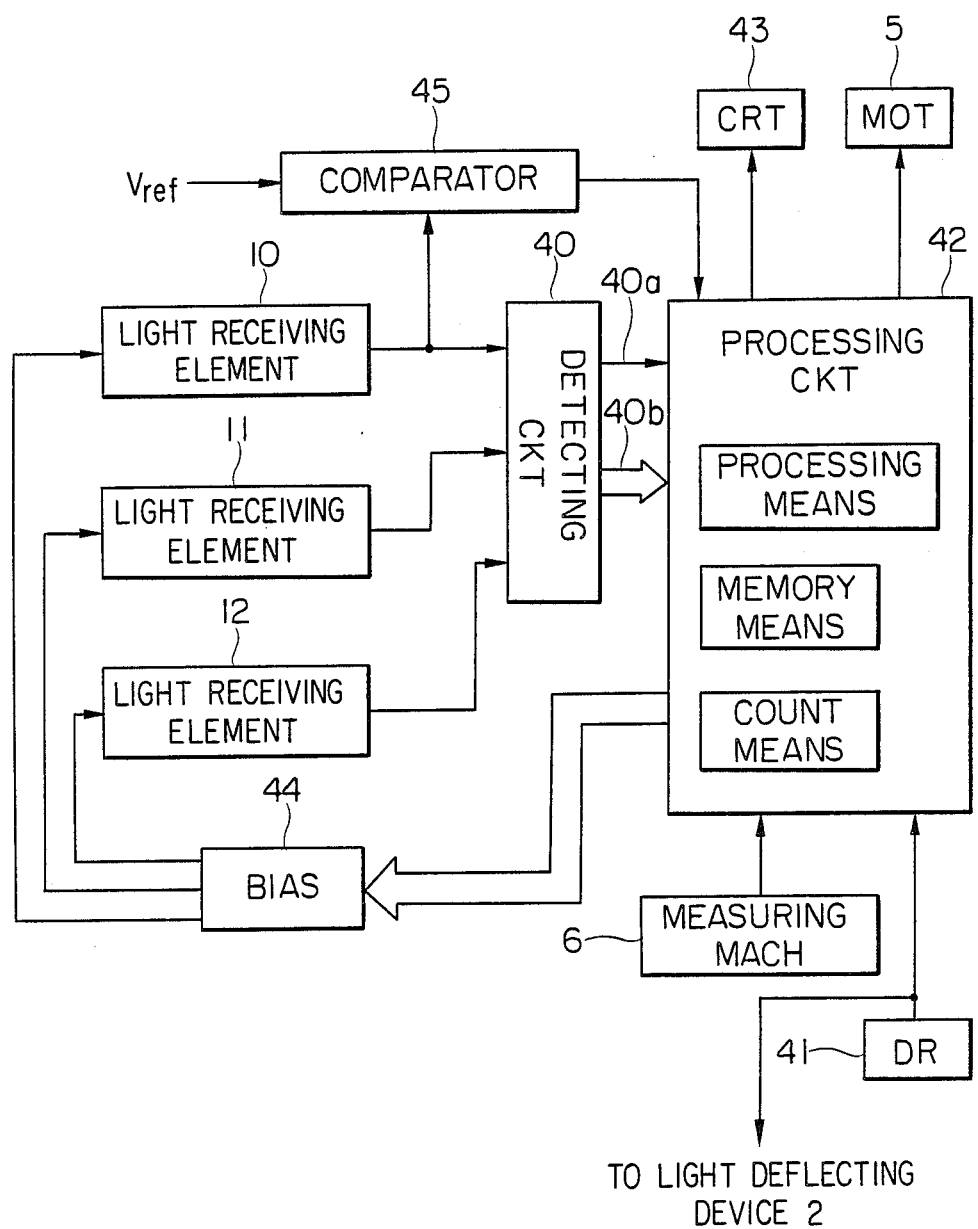
FIG. 3 is a circuit block diagram of the FIG. 1 apparatus.

FIG. 1 is a perspective view schematically showing the construction of a foreign substance inspecting system suitable for an embodiment of the present invention. The basic construction of such system is the same as that of the apparatus disclosed in detail in U.S. Pat. No. 4,468,120 and therefore will be described simply herein. Laser light $1a$ from a laser light source 1 is deflected by a predetermined angle in x direction by a light deflecting device (such as a vibratory mirror) 2 and is focused as a light spot on the surface (upper surface) of a mask M through an imaging lens 3. In FIG. 1, the angle of incidence of the laser light $1a$ passing from the light deflecting device 2 to the mask M is determined to 70°-80° (20°-30° from the surface of the mask M) with the influence of the circuit pattern of the mask M being taken into account. With the aid of the action of the light deflecting device 2, the light spot of the laser light $1a$ scans the surface of the mask M along a scanning track 1 extending substantially rectilinearly in x direction. The mask M is placed on a slider 4 so that the surface thereof is parallel to xy plane. The slider 4 is of such a frame-like shape which holds only the marginal portion of mask M, and is moved in y direction (the direction of arrow A) orthogonal to x direction by a motor 5. With the aid of the light deflecting device 2 and the slider 4, the light spot of the laser light $1a$ two-dimensionally scans (raster-scans) the surface of the mask M. Now, at three locations which subtend the scanning track 1 on the surface of the mask M from different directions, there are disposed light receiving elements (such as photomultipliers) 10, 11 and 12 serving as photoelectric converting means. Condensing lenses $10a$, $11a$ and $12a$ for efficiently condensing scattered light produced from the scanning track 1 on light receiving surfaces are disposed forwardly of the light receiving elements 10, 11 and 12, respectively. The optic axes $l_1$, $l_2$ and $l_3$ of the respective condensing lenses $10a$, $11a$ and $12a$ are determined so as to be at a small angle (5°-45°) with respect to the surface of the mask M and so as to intersect the center of the scanning track 1 in x direction. The projected image of the optic axis $l_1$ onto xy plane is coincident with the scanning track 1, and the projected images of the optic axes $l_2$ and $l_3$ onto xy plane are determined so as to be at a predetermined angle (30°-45°) with respect to the scanning track 1 and so that the optic axes $l_2$ and $l_3$ are substantially plane-symmetrical with respect to Y-Z plane. The position of the slider 4 in y direction is detected by a measuring machine 6 such as a linear encoder.

Now, in the present apparatus, a reference index plate 20 comprising a planar glass plate whose length in x direction is of the same extent as the width of the mask M (or the length of the scanning track 1) and whose thickness is of the same extent as that of the mask M is provided on the fore end side of the slider 4. The surface of the reference index plate 20 is determined so as to be flush with the surface of the mask M. In the present embodiment, a solid substance 30 comprising a thin film of chromium or the like having the same size as the standard size of a foreign substance to be detected and smaller than the size (1 $\mu$m-100 $\mu$m) of the light spot of the laser light 1a on the scanning track 1 and having a thickness of the order of 0.1 $\mu$m-10 $\mu$m is fixed as a reference pattern on the glass surface (the laser light incidence side) of the reference index plate 20. In FIG. 2, the solid substance 30 is rectangular, but alternatively, it may be of another shape such as a circle. When the spot of the laser light 1a is supplied to the solid substance 30, scattered light is produced in various directions from all of the level difference edge portions of the concavo-concavity of the reference index plate 20 and the solid substance 30. That is, scattered light similar to the scattered light from the foreign substance is produced. If the solid substance 30 as shown in FIG. 2 is provided at one location on the reference index plate 20, it will be sufficient with respect to a simple measurement of the light reception sensitivity of the light receiving elements 10, 11 and 12, but where the light reception sensitivity measurement corresponding to the scanning position of the spot of the laser light 1a, i.e., the position in x direction on the scanning track 1, is also to be effected, a plurality of solid substances 30 may be arranged at a predetermined interval in x direction.

FIG. 3 is a simple block diagram of the signal processing circuit of the present apparatus. The photoelectric signals from the three light receiving elements 10, 11 and 12 are input to a detecting circuit 40. The detecting circuit 40, as disclosed in detail in U.S. Pat. No. 4,468,120, discriminates the scattered light from the circuit pattern such as chromium on the mask M and the scattered light from the foreign substance, and puts out a detection signal 40a when the spot of the laser light 1a irradiates the foreign substance. Further, the detecting circuit 40 also puts out quantity-of-light information 40b corresponding to the quantity of scattered light from the detected foreign substance. This quantity-of-light information 40b is used to recognize the size of the foreign substance. A driving circuit 41 puts out a scanning signal for laser light scanning to the light deflecting device 2. It is to be understood that the scanning signal corresponds to the position of the spot light in x direction on the scanning track 1. Now, this scanning signal, the detection signal 40a, the quantity-of-light information 40b and the position information from the measuring machine 6 are input to a central processing circuit (such as a digital computer) 42. Each time the detection signal 40a is produced, the central processing circuit 42 stores the then quantity-of-light information 40b, the position information in x direction based on the scanning signal and the position information in y direction from the measuring machine 6 successively in memory means. After the scanning of the laser light 1a has been terminated with respect to the whole surface of the mask M, the processing means of the central processing circuit 42, on the basis of the information stored therein, causes a display device (CRT) 43 to display the position on the mask M to which the foreign substance adheres and the information (for example, divided into classes A, B, C, etc.) obtained by ranking the size of the foreign substance by a statistical technique. Also, the central processing circuit 42 drives the motor 5 so as to control the moved position on the slider 4 in y direction on the basis of the position information from the measuring machine 6. In the present embodiment, it is to be understood that the light receiving elements 10, 11 and 12 are comprised of photomultipliers. So, a biasing circuit 44 (sensitivity calibrating means) capable of varying a high voltage applied as a bias to the photomultipliers by a command from the central processing circuit 42 is provided to adjust the light reception sensitivity of the light receiving elements 10, 11 and 12. A comparator 45, in order to detect the size of the spot light, puts out to the central processing circuit 42 a high level signal when the output from the light receiving element 10 during the scanning of the laser light exceeds a predetermined level indicated by Vref, and a low level signal when said output is below the predetermined level. Where the light receiving elements 10, 11 and 12 are solid state light receiving elements (such as photodiodes), if the photoelectric signals are amplified by variable gain amplifiers and a gain control circuit for adjusting the gain of each variable gain amplifier is provided instead of the biasing circuit 44, adjustment of the light reception sensitivity can be effected in a similar manner. By such adjustment of the light reception sensitivity, the magnitude of the quantity-of-light information 40b obtained when the laser light 1a irradiates the same foreign substance or the solid substance 30 on the reference index plate 20 is varied.

Figure 4:
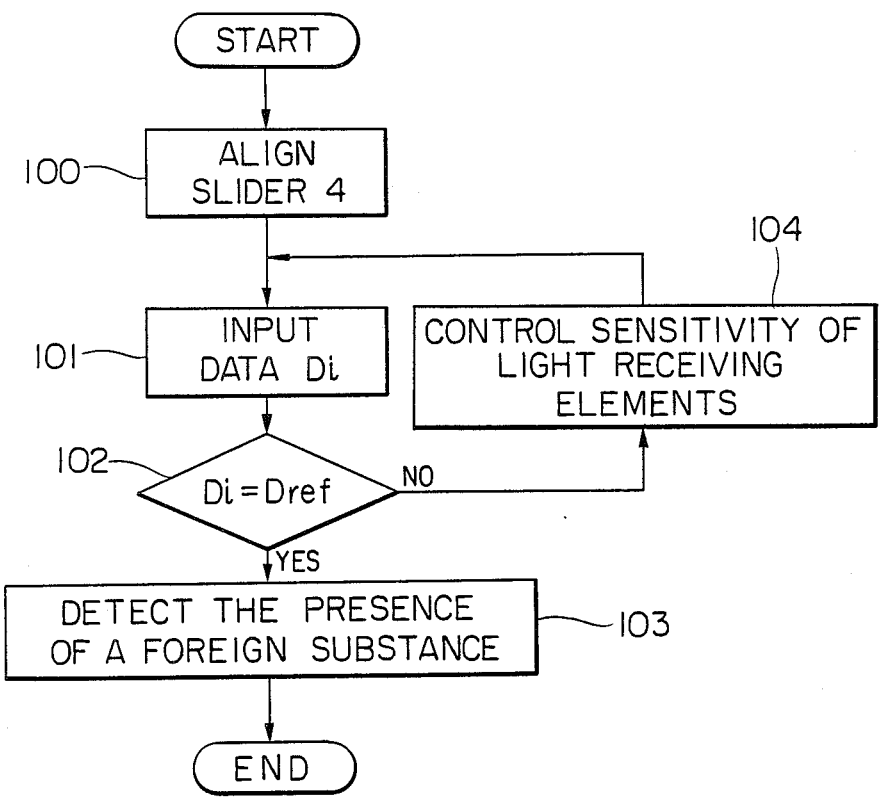
FIG. 4 is a flow chart of the operation of adjusting the foreign substance detection accuracy.

The operation of the present invention will now be described by reference to the flow chart of FIG. 4. Steps 100, 101, 102 and 104 in FIG. 4 are operations which take place before a foreign substance on the mask M is inspected. It is to be understood that during the manufacture of the apparatus, after the light reception sensitivity has been adjusted in accordance with the size of an actual foreign substance, the quantity-of-light information 40b corresponding to the scattered light produced from the solid substance 30 is stored as data Dref in the memory means of the control processing circuit 42.

After the mask M has been placed on the slider 4 as shown in FIG. 1, the central processing circuit 42 effects at step 100 the positioning of the slider 4 in y direction so that the scanning track 1 of the laser light 1a comes to lie at a predetermined position across the solid substance 30 on the reference index plate 20. Subsequently, at step 101, the central processing circuit 42 inputs as data Di the quantity-of-light information 40b corresponding to the photoelectric signals of the three light receiving elements 10, 11 and 12 which correspond to the scattered light from the solid substance 30, and at step 102, it compares the quantity-of-light indicated by the data Di with the quantity-of-light indicated by the prestored data Dref. When, in this comparison, there is no difference with respect to the three light receiving elements 10, 11 and 12, the foreign substance detection sensitivity does not change from its initial value (the value during the manufacture of the apparatus) and therefore, the central processing circuit 42 executes the next step 103. If there is a difference at this step 102, the central processing circuit 42 adjusts the bias voltage of the photomultipliers through the biasing circuit 44 at step 104 to change the light reception sensitivity of the light receiving elements 10, 11 and 12 to the intended value. Then the central processing circuit 42 again repeats a similar operation from step 101.

Now, when it is judged at step 102 that the light reception sensitivity of the light receiving elements 10, 11 and 12 has been adjusted to the intended value, the central processing circuit 42 feeds the slider 4 in y direction at a predetermined speed at step 103 and the whole surface of the mask M is raster-scanned by the spot of the laser light 1a. If during this scanning, there is a foreign substance on the mask M, the central processing circuit 42 stores therein the position of the foreign substance in x and y directions (coordinates value) and the quantity-of-light information 40b relating to the size of the foreign substance in succession. At a point of time whereat the scanning of the slider 4 in y direction has been terminated, the central processing circuit 42 displays the position of the foreign substance and the ranked classifications (A, B, C, etc.) as previously described.

Also, if a plurality of solid substances 30 according to the present embodiment are provided at a predetermined interval in x direction on the reference index plate 20, the foreign substance detection sensitivity can be adjusted in conformity with the scanning position on the scanning track 1 (the position in x direction). In this case, the quantity-of-light information 40b corresponding to the scattered light from each of the plurality of solid substances is pre-stored during the manufacture of the apparatus and, each time foreign substance inspection is effected, the reference index plate 20 is scanned by the laser light 1a and any deviation of the foreign substance detection sensitivity in x direction from that during the manufacture is detected. Where any deviation (difference) of the detection sensitivity occurs with respect to the position in x direction, the deviation is corrected by software or the like so that the central processing circuit 42 judges while allowing for the deviation of the detection sensitivity corresponding to the coordinates value of the foreign substance in x direction when it judges (classifies) the size of the foreign substance. Also, as regards the hardware, as disclosed in U.S. Pat. No. 4,468,120, an amplifier for varying the amplification rate of the photoelectric signal from each light receiving element 10, 11, 12 in synchronism with the scanning position of the laser light 1a in x direction may be provided and the variation characteristic of the amplification rate of the amplifier may be changed so as to correct the deviation of the foreign substance detection sensitivity with respect to x direction. The solid substance 30 in the present embodiment is planarly glued to a glass surface, but even a cubic substance such as fine powder of glass may result in a similar effect.

As described above, in the apparatus suitable for the present embodiment, the three light receiving elements 10, 11 and 12 are disposed so as to subtend the laser light incidence side surface of the mask M from different directions, but where the circuit pattern is not complicated or in the case of blank glass or the like having no circuit pattern, the light receiving elements may be provided at two locations or at only one location. Also, if the present invention is applied to an apparatus in which, as disclosed in U.S. Pat. No. 4,468,120, a pair of light receiving elements are disposed symmetrically on the upper surface side and the lower surface side of a mask M and the scattered light produced on the upper surface side is compared with the scattered light produced on the lower surface side to thereby accurately judge the state of adherence of foreign substances and detect only the foreign substance which will truly do injury during the exposure, an entirely similar effect may be obtained. In such case, the optical path may be changed over by an optical path change-over mirror or the like so that the laser light 1a may enter from the back surface (lower surface) of the mask M, thereby inspecting foreign substances adhering to the back surface. Thus, a solid substance 30 similar to that of FIG. 2 may be provided also on the back surface of the reference index plate 20 shown in FIG. 1 and by the use of it, the adjustment of the light reception sensitivity of the light receiving element which subtends the lower surface side of the mask M may be effected in a procedure similar to that in the present embodiment. Also, in such an apparatus of the type wherein the scattered light produced on the upper and lower surface sides of the mask M are compared with each other, by the utilization of the fact that the reference index plate 20 is transparent, the scattered light produced on the upper and lower surface sides from the solid substance 30 may be detected and the light reception sensitivity may be adjusted so that the ratio between the photoelectric signals of the light receiving element subtending the upper surface side and the light receiving element subtending the lower surface side may be an intended value. This also holds true of an apparatus in which regularly reflected light produced on the upper surface on the laser light incidence side of the mask M is compared with light transmitted to the back surface to thereby detect an opaque foreign substance. The design may be such that the laser light 1a enters the mask M perpendicularly thereto, and also, the present invention may be applied to an apparatus of the type in which the laser light 1a is endowed with a polarization characteristic, a polarizing filter is provided in front of each light receiving element and only a foreign substance is detected by the utilization of the fact that the polarized state of the scattered light or the reflected light from the circuit pattern and the polarized state of the scattered light from the foreign substance differ from each other, to thereby obtain a similar effect.

Figure 5:
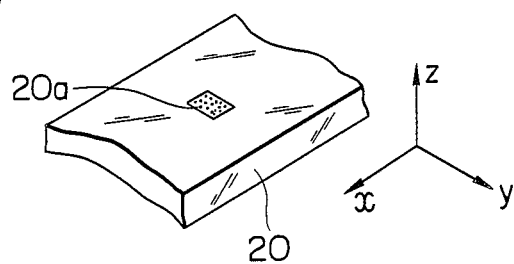
FIG. 5 is a fragmentary perspective view showing a reference pattern according to a second embodiment of the present invention.

FIG. 5 is a fragmentary perspective view of a reference index plate 20 provided with a reference pattern according to a second embodiment of the present invention. In the present embodiment, a diffusing portion (ground glass) 20a of the same size and shape as the solid substance 30 of FIG. 2 is formed on the glass surface of the reference index plate 20. Such a diffusing portion 20a can be easily made by etching or machining. The diffusing portion 20a is better in laser light scattering property (weaker in the directionality of scattered light) than the solid substance 30 and can reproduce a state approximate to the state of occurrence of the scattered light from an actual foreign substance. If a plurality of such diffusing portions, like a plurality of solid substances 30, are provided in x direction or provided also on the back surface of the reference index plate 30, there will be obtained an effect similar to that of the first embodiment. Also, if the diffusing portion 20a is made into the form of a slit elongated in x direction, any irregularity of the foreign substance detection sensitivity conforming to the x direction scanning position of the spot light can be detected precisely.

Figure 6:
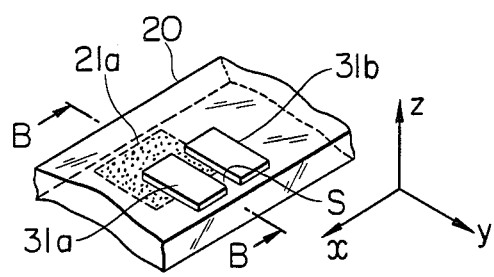
FIG. 6 is a fragmentary perspective view showing a reference pattern according to a third embodiment of the present invention.

FIG. 6 is a fragmentary perspective view of a reference index plate 20 provided with a reference pattern according to a third embodiment of the present invention. In this embodiment, the spot size and intensity of the laser light which are a factor which affects the foreign substance detection sensitivity are also detected. Light-intercepting thin films 31a and 31b such as chromium formed in a rectangular shape are provided adjacent to each other in x direction on the laser light incidence side glass surface of the reference index plate 20. A slit S having a width smaller than the spot size of the laser light 1a is formed between the thin films 31a and 31b in x direction. The total size of the thin films 31a and 31b is determined to a value greater than the spot size. A rectangular diffusing portion 21a is formed on the back surface of the reference index plate 20 correspondingly to the position of the slit S in x direction. The diffusing portion 21a is of the same function as the diffusing portion 20a of FIG. 5, but in the present embodiment, it may be of a size in accord with the spot size. Also, the portion of the diffusing portion 21a in y direction is shifted from the position of the slit S in y direction. The amount of shift of the diffusing portion 21a in y direction is made to correspond to the angle of incidence of the laser light 1a by taking into account that the laser light 1a obliquely enters the reference index plate 20. In the present embodiment, there is also a characteristic that the quantity of scattered light from the diffusing portion 21a can be freely adjusted by changing the width of the slit S.

Figure 7:
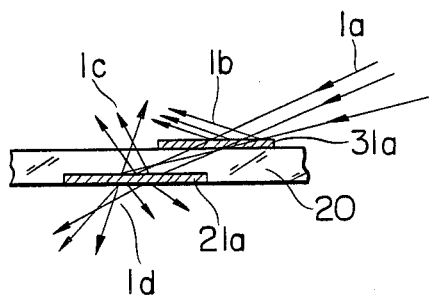
FIG. 7 is a cross-sectional view taken along line B—B of FIG. 6.

Now, in such construction, when the spot of the laser light 1a scans the reference index plate 20 in x direction, as shown in FIG. 7, the laser light 1a transmitted through the slit S irradiates the diffusing portion 21a of the back surface when the light spot crosses the thin films 31a and 31b, and scattered light 1c and 1d is produced on the upper surface side (laser incidence side) and the lower surface side, respectively, of the reference index plate 20. Since the width of the slit S is smaller than the spot size, the time-serial distribution of the quantity-of-light of the laser light 1a transmitted through the slit S and scattered by the diffusing portion 21a during the scanning, that is, the period during which scattered light exceeding a predetermined quantity is produced during the scanning, corresponds to the distribution of the intensity of light of the spot light in x direction on the surfaces of the thin films 31a and 31b or the spot size. Accordingly, the quantities of the scattered light 1c and 1d from the diffusing portion 21a also correspond to it, and the photoelectric signal wave forms (peak waves) of the three light receiving elements 10, 11 and 12 also correspond to the spot size in x direction or the intensity of light. Thus, to measure the spot size, the photoelectric signal of the light receiving element 10 shown in FIG. 3 is input to the comparator 45, which compares the photoelectric signal with Vref, and the count means of the processing circuit 42 measures the time range in which the scattered light 1c and 1d is produced at a certain level or higher. On the basis of this time range and the scanning speed of the spot of the laser light 1a on the reference index plate 20 pre-stored in memory means, the processing means of the processing circuit 42 determines the spot size. Also, the intensity of the laser light 1a can be measured form the peak value of the photoelectric signal.

As is apparent from the above-described operation, the thin films 31a and 31b are determined to such a size that during the scanning of the laser light 1a in x direction, they transmit only a part of the light spot therethrough and reflect (reflected light 1b) most of the spot light and therefore, for the following reason, it is more convenient to determine the width of the diffusing portion 21a in x direction to a value smaller than or equal to the full width of the thin films 31a and 31b in x direction.

That is, when the laser light 1a irradiates the diffusing portion 21a of the back surface before the light spot is intercepted by the thin film 31a or 31b, an excessive scattered light is produced in addition to the scattered light 1c and 1d produced as a result of the laser light being transmitted through the slit S, and not only measurement of the intensity of light and the spot size becomes difficult, but also there occurs an inconvenience that the light receiving elements are fatigued. However, where there is not produced such a degree of scattered light that fatigues the light receiving elements, the width of the diffusing portion 20a may be made great relative to the full width of the thin films 31a and 31b in x direction. In this case, of the time-serial photoelectric signals produced during a scanning period of the light spot, the signal other than the signals of the portions corresponding to the scanning positions of the thin films 31a and 31b may be electrically masked so as not to be detected.

If a construction comprising such thin films 31a, 31b and the diffusing portion 21a is provided at each of a plurality of positions on the reference index 30 in x direction, any variation in the intensity of light and the spot size corresponding to the scanning position of the laser light 1a in x direction can be quantitatively detected. Where the spot size of the light spot becomes larger than a predetermined value (the value during the manufacture and adjustment) and thereby the intensity of the light spot becomes weak, the foreign substance detection sensitivity may be corrected in accordance with the variation in the intensity of light. More specifically, as in the first embodiment, the light reception sensitivity of the light receiving elements 10, 11 and 12 may be re-adjusted or, in a software-like fashion, the decision standard (ranking) of the size of the foreign substance may be corrected. Of course, as in the first and second embodiments, the scattered light 1c and 1d may be detected and used only to adjust the light reception sensitivity of the light receiving elements.

In the case of a reference pattern in which the intensity and spot size of the light spot can be detected, the reference index plate 20 having that reference pattern may extend in the direction of movement of the slider 4, i.e., y direction. In this case, the reference index plate is disposed so that during the movement of the slider 4, the reference pattern is scanned near the scanning starting point or terminating point of the spot light in x direction. When, in this manner, the intensity of light and the spot size are detected correspondingly to the scanning position in y direction, the stability of rectilinear movement of the slider 4 in vertical direction (z direction) can be detected. Therefore, the irregularity of the foreign substance detection sensitivity in y direction can be corrected as well as in x direction. Also, the slit S may extend in x direction. Instead of the slit S, only a diffusing portion 21a having a width equal to the width of the slit S may be provided.

Figure 8:
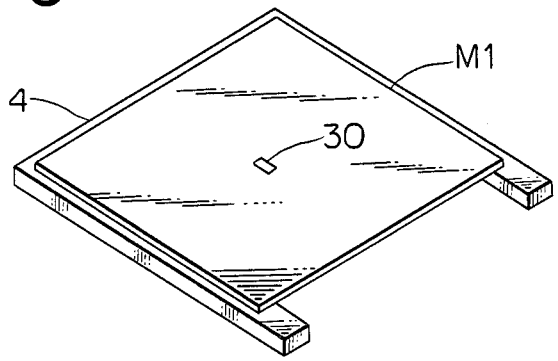
FIGS. 8 and 9 are fragmentary perspective views showing fourth and fifth embodiments, respectively, of the present invention.
Figure 9:
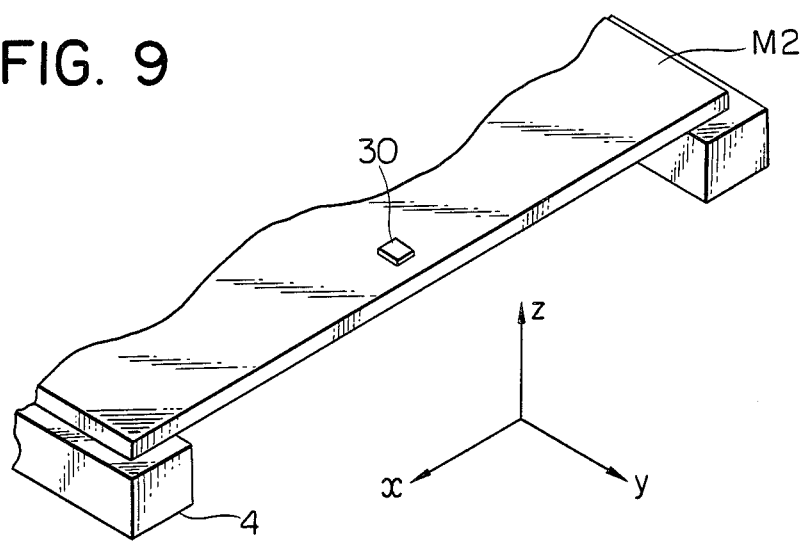

Referring now to FIG. 8, there is shown an embodiment in which a reference pattern such as a solid substance 30, thin films 31a, 31b and a diffusing portion 20a or 21a is directly formed on an ordinary glass plate M1 on which no circuit pattern is formed. However, the solid substance 30 is taken as an example of the reference pattern. In the case as shown in FIG. 9, the reference pattern is provided around the effective exposure area of a mask M2. Particularly, where the thin films 31a, 31b and diffusing portion 21a are to be provided as in the third embodiment, the film films 31a and 31b together with a circuit pattern may be provided on the same surface as the surface of the mask on which the circuit pattern is formed (the pattern surface). Also, if a solid substance 30, a diffusing portion 20a or 21a and thin films 31a, 31b are disposed at a plurality of two-dimensional positions on a test mask (test reticle) made for checking the resolving power, the superposition accuracy, etc. of a projection exposure apparatus and inspection is effected with this test mark being placed on the slider 4, there will be obtained a similar effect. If a reference pattern is provided on the reference index plate 20 and this is fixed to the slider 4, there will be an advantage that even if the mask M is absent, the foreign substance detection sensitivity can be checked when required. Also, the value of the spot size of the laser light in y direction can be easily found by detecting the width of the peak wave form of the photoelectric signal during each spot scanning while moving the slider 4. Further, also by the reference patterns (solid substance 30 and diffusing portion 20a) according to the first and second embodiments of the present invention, the spot size and the intensity of light can be measured on the basis of the quantity of scattered light as in the third embodiment. Thus, if a plurality of such reference patterns are provided in x and y directions and the spot size at each position is measured, the inclination of the movement plane of the slider 4 (the surface of the mask M) relative to xy plane can be detected. Therefore, by manually or automatically adjusting the positions of optical elements (a lens, a light deflecting device, etc.) in the laser light 1a supplying optical system in accordance with said inclination, the light spot can be accurately imaged with a minimum spot size at all positions on the whole surface of the mask M, and the foreign substance detection sensitivity can be stabilized.

Figure 10:
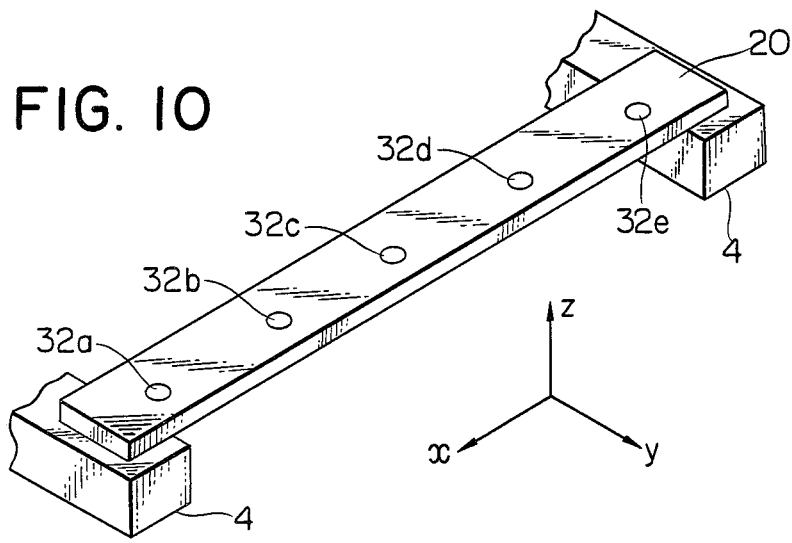
FIG. 10 is a fragmentary perspective view showing a sixth embodiment of the present invention.

FIG. 10 shows an embodiment in which light-emitting diodes (hereinafter referred to as LEDs) 32a, 32b, 32c, 32d and 32e producing the same degree of light of predetermined brightness as the scattered light from a standard foreign substance to be detected with weak directionality (or without directionality) are provided as reference light sources on a reference index plate 20. It is desirable that the light-emitting points of LEDs 32a–32e be positioned in the same plane as the surface of the mask M, but this is not always necessary. If one such LED is provided at a location on the plate 20, it will be sufficient for simple measurement of the light reception sensitivity of the light receiving elements 10, 11 and 12, but in the present embodiment, with a case where the measurement of the light reception sensitivity corresponding to the scanning position of the spot of the laser light 1a, i.e., the position in x direction on the scanning track 1 is also effected being taken into account, five LEDs 32a, 32b, 32c, 32d and 32e are arranged at a predetermined interval in x direction.

Figure 11:
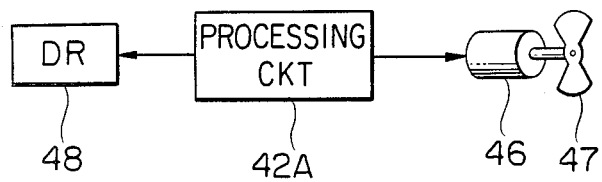
FIG. 11 is a circuit block diagram of the sixth embodiment.

FIG. 11 shows a block diagram of the FIG. 10 embodiment. The light receiving elements 10, 11 and 12, the biasing circuit 44, the detecting circuit 40, the measuring machine 6, the driving circuit 41, the CRT 43, the motor 5 and the comparator 45 may be similar to those shown in FIG. 3 and therefore are omitted. A drive circuit 48 includes a circuit for keeping the brightness of the five LEDs 32a–32e constant and also has the function of determining the LED to be turned on, by the command from the central processing circuit 42. A shutter 47 driven by a motor 46 intercepts light so that the laser light 1a does not enter the mask M during the sensitivity adjustment by the LEds, and is disposed between the light source 1 and the light deflecting device 2.

A central processing circuit 42A has, in addition to the function of the circuit 42 of FIG. 3, the function of controlling the drive circuit 48 and the motor 46. The central processing circuit 42A, during its initial setting, causes the LEDs 32a–32e to emit light on the scanning track 1 and also stores therein the magnitudes (the initial light reception sensitivity values) of the then photoelectric signals of the LEDs 10, 11 and 12.

Adjustment of the light reception sensitivity (the foreign substance detection sensitivity) will now be described. Prior to the inspection of a foreign substance, the central processing circuit 42A positions the slider 4 so that the LEDs 32a–32e are positioned on the scanning track 1. Subsequently, the shutter 47 is closed so that the laser light 1a does not irradiate the plate 20. Then, the central processing circuit 42A actuates the drive circuit 45 to cause the five LEDs 32a–32e to emit light in succession at a predetermined timing for a predetermined time. During the light emission of the LEDs 32a–32e, the central processing circuit 42A detects and stores the quantity-of-light information 40b corresponding to the magnitude of each of the photoelectric signals of the light receiving elements (photomultipliers) 10, 11 and 12. Thereafter, the central processing circuit 42A compares the pre-stored initial light reception sensitivity value of each light receiving element with the detected quantity-of-light information 40b and detects how much the light reception sensitivity has been varied.

On the basis of the amount of variation in the light reception sensitivity, the central processing circuit 42A calculates the amount of correction relative to the pre-stored initial set value of the bias voltage of the photomultipliers by a predetermined calculation, and controls the biasing circuit 44 so that the bias voltage varies by that amount of correction. The LEDs 32a–32e may be again caused to emit light when this bias adjusting operation has been terminated, whereby whether the sensitivity adjustment has been effected properly may be checked.

When the sensitivity adjustment (calibration) has been terminated in the above-described manner, the shutter 47 may be opened and the slider 4 may be intactly moved in y direction to thereby start the inspection of the foreign substance on the mask M.

Also, if the light reception sensitivity of the light receiving elements 10, 11 and 12 is only calibrated as described above, it is not necessary to cause all of the five LEDs 32a–32e to emit light, but for example, only the middle LED 32c may be caused to emit light. Now, when the light reception sensitivity of each light receiving element in the direction of the scanning track 1, i.e., the distribution of the foreign substance detection sensitivity in x direction, is to be detected, for example, the light emission brightnesses of the LEDs 32a–32e are made uniform and with respect to each light receiving element, the quantity-of-light information by the light from the LEd 32a, the quantity-of-light information by the light from the LED 32b, . . . are successively detected in accordance with the light emission timings of the respective LEDs, and are compared with the pre-stored initial light reception sensitivity value. If this is done, how much the sensitivity distribution of each light receiving element in x direction has varied from the initial setting can be immediately known. If there occurs a variation in the sensitivity distribution in x direction, the correction curve of sensitivity correcting means provided in the detecting circuit 40 to vary the gain of the amplifier or the reference level of the comparator in accordance with the scanning position of the spot of the laser light may be adjusted as disclosed in U.S. Pat. No. 4,468,120.

In the above-described embodiments, the foreign substance detection sensitivity is adjusted by changing the light reception sensitivity of the light receiving elements 10, 11 and 12, but alternatively, when the central processing circuit 42A is to rank the sizes of foreign substances and display the same on a display device 43, the standard of the ranking may only be adjusted in accordance with the quantity-of-light information 40b by the light emission of the LEDs. In this case, when the detected quantity-of-light information 40b is one half, for example, relative to the pre-stored initial light reception sensitivity value, if the standard (level) of the ranking is made ½, the display will not change. Also, changing the level of the ranking in this manner can be easily carried out by two-dimensionally scanning the spot of the laser light by the mask M for the purpose of foreign substance inspection and storing all the quantity-of-light information 40b corresponding to the foreign substance, and thereafter processing the same in a software-like fashion. Therefore, the sensitivity correction corresponding to the scanning position of the spot of the laser light in x direction is also possible simply by the adjustment of the level of the ranking during the display. Moreover, according to the software-like adjustment of the sensitivity, adjustment can be easily accomplished with respect not only to the sensitivity distribution in x direction but also to the sensitivity distribution in y direction.

According to the present embodiment, as described above, LEDs are provided on the portion other than the portion of the slider 4 which holds the mask M and therefore, sensitivity adjustment can be accomplished by only the movement of the slider 4 immediately before the foreign substance inspection. Further, there is an advantage that the light reception solid angle or the like or each light receiving element can be checked by reading the quantity-of-light information 40b while causing the LEDs to emit light and moving the slider 4 in y direction.

Also, it is desirable that the LEDs produce light of a wavelength identical or approximate to the wavelength of the laser light (light beam) for foreign substance inspection. However, where there is available no LED which produces light of a wavelength approximate to the wavelength of the laser light, a combination of a white lamp and a color temperature converting filter may be provided on the plate 20 so that there may be obtained reference light of a wavelength approximate to the wavelength of the laser light. Further, the reference light sources such as LEDs need not always be provided directly on the plate 20, but one end surface of a light transmission cable such as glass fiber may be opposed to the light sources and the other end surface thereof may be embedded in the plate 20 and that other end surface may be made to shine.

What is claimed is:

1. An apparatus for inspecting a foreign substance on a surface of an object to be inspected, said apparatus comprising:
   (a) disposing means for disposing said object on a predetermined area of said disposing means with the surface of said object substantially in a predetermined plane;
   (b) scanning means for generating a radiation beam, focusing a spot of said radiation beam on said predetermined plane, and scanning the surface of said object disposed on said disposing means with said radiation beam, said foreign substance scattering radiation from said radiation beam;
   (c) a device including a transmitting member scanned by said radiation beam and transmitting radiation from said radiation beam therethrough, intercepting means disposed on one surface of said transmitting member at one side thereof for intercepting said radiation beam, and a scattering portion disposed on another surface of said transmitting member at an opposite side thereof with respect to said one surface, said transmitting member being mounted on an area of said disposing means different from said predetermined area with said one surface substantially in said predetermined plane, said intercepting means permitting radiation from said radiation beam to transmit through a spatial interval on said one surface of said transmitting member, said spatial interval having a width narrower than the width of said radiation beam in a scanning direction of said scanning means, said scattering portion receiving radiation from said radiation beam passed through said spatial interval, scattering the received radiation, and producing a quantity of scattered radiation which is substantially similar to the quantity of the radiation scattered by said foreign substance;
   (d) detecting means for detecting the scattered radiation and producing a detection signal; and
   (e) control means for adjusting said detecting means in response to the detection signal produced by the radiation scattered by said scattering portion.

2. An apparatus according to claim 1, wherein said intercepting means has two intercepting members that are spaced along said scanning direction so that said spatial interval is formed, and wherein said transmitting member is a plate.

3. An apparatus according to claim 2, wherein said scattering portion is shifted relative to said two intercepting members along a direction perpendicular to said scanning direction.

4. An apparatus according to claim 3, wherein said detecting means has comparing means for comparing said detection signal with a predetermined level, and said control means changes said predetermined level in response to the detection signal produced by radiation scattered by said scattering portion.

5. An apparatus for inspecting a foreign substance on a surface of an object to be inspected, said apparatus comprising:
   (a) disposing means for disposing said object on a predetermined area of said disposing means with the surface of said object substantially in a predetermined plane;
   (b) scanning means for generating a radiation beam focusing a spot of said radiation beam on said predetermined plane, and scanning the surface of said object disposed on said disposing means with said radiation beam, said foreign substance scattering radiation from said radiation beam;

(c) a device including a transmitting member scanned by said radiation beam and transmitting radiation from said radiation beam therethrough, intercepting means disposed on one surface of said transmitting member at one side thereof for intercepting said radiation beam, and a scattering portion disposed on another surface of said transmitting member at an opposite side thereof with respect to said one surface, said transmitting member being disposed by said disposing means on said predetermined area with said one surface substantially in said predetermined plane, said intercepting means permitting radiation from said radition beam to transmit through a spatial interval on said one surface of said transmitting member, said spatial interval having a width narrower than the width of said radiation beam in a scanning direction of said scanning means, said scattering portion receiving radiation from said radiation beam passed through said spatial interval, scattering the received radiation, and producing a quantity of scattered radiation which is substantially similar to the quantity of the radiation scattered by said foreign substance;

(d) detecting means for detecting the scattered radiation and producing a detection signal; and (e) control means for adjusting said detecting means in response to the detection signal produced by the radiation scattered by said scattering portion.

6. An apparatus according to claim 5, wherein said intercepting means has two intercepting members that are spaced along said scanning direction so that said spatial interval is formed, and wherein said transmitting member is a plate.

7. An apparatus according to claim 6, wherein said scattering portion is shifted relative to said two intercepting members along a direction perpendicular to said scanning direction.

8. An apparatus according to claim 7, wherein said detecting means has comparing means for comparing said detection signal with a predetermined level, and said control means changes said predetermined level in response to the detection signal produced by radiation scattered by said scattering portion.

* * * * *